(12) United States Patent
Graham et al.

(10) Patent No.: US 10,107,811 B2
(45) Date of Patent: Oct. 23, 2018

(54) DETECTION OF SPECIFIC ANTIGENS IN A POPULATION OF ANTIGENS

(71) Applicants: Henry A. Graham, Solana Beach, CA (US); John G. Gorman, Del Mar, CA (US); James P. Rowell, Stockton, NJ (US)

(72) Inventors: Henry A. Graham, Solana Beach, CA (US); John G. Gorman, Del Mar, CA (US); James P. Rowell, Stockton, NJ (US)

(73) Assignee: Chrome Red Technologies, LLC, Stockton, NJ (US)

( * ) Notice: Subject to any disclaimer, the term of this patent is extended or adjusted under 35 U.S.C. 154(b) by 115 days.

(21) Appl. No.: 14/756,975

(22) Filed: Nov. 4, 2015

(65) Prior Publication Data

US 2016/0069877 A1   Mar. 10, 2016

Related U.S. Application Data

(62) Division of application No. 13/385,428, filed on Feb. 21, 2012, now Pat. No. 9,182,389.

(60) Provisional application No. 61/463,738, filed on Feb. 22, 2011.

(51) Int. Cl.

| | | |
|---|---|---|
| *G01N 33/80* | (2006.01) | |
| *G01N 33/569* | (2006.01) | |
| *G01N 33/541* | (2006.01) | |
| *G01N 33/537* | (2006.01) | |
| *G01N 33/53* | (2006.01) | |
| *G01N 33/543* | (2006.01) | |

(52) U.S. Cl.
CPC ... *G01N 33/56966* (2013.01); *G01N 33/5304* (2013.01); *G01N 33/537* (2013.01); *G01N 33/541* (2013.01); *G01N 33/54326* (2013.01); *G01N 33/80* (2013.01); *G01N 2333/705* (2013.01); *G01N 2446/00* (2013.01)

(58) Field of Classification Search
CPC .. G01N 21/648; G01N 33/537; G01N 33/541; G01N 33/5304; G01N 33/54306; G01N 33/54326; G01N 33/56966; G01N 33/80; G01N 2333/705; G01N 2446/00
See application file for complete search history.

(56) References Cited

U.S. PATENT DOCUMENTS

| | | | | |
|---|---|---|---|---|
| 4,925,786 A | * | 5/1990 | Uthemann | G01N 33/80 435/7.25 |
| 5,646,004 A | * | 7/1997 | Van Vlasselaer | B01L 3/5021 210/781 |
| 7,998,696 B2 | * | 8/2011 | Zaugg | G01N 33/491 422/412 |

* cited by examiner

*Primary Examiner* — Gailene Gabel
(74) *Attorney, Agent, or Firm* — Ralph T. Lilore

(57) ABSTRACT

Methods for detecting the presence or absence of, and for quantifying, one set of cells in a mixed cell population of at least two sets of cells especially Rh positive cells in a mixed population with Rh negative cells, as is found in a fetal maternal hemorrhage (FMH).

The magnetic particles coated with anti-D antibodies are reacted with the Rh positive fetal cells in Rh negative maternal blood followed by a specific separation and quantifying technique.

Gravitational forces or magnetic forces are used to move reacted magnetic particles to isolate, distinguish and quantify cells differentiated by antigenic composition.

Rh positive cell volume is correlated to the volume of the original blood sample as an indication of the number of doses of RhIG needed to be administered to the mother to prevent subsequent Rh immunization.

17 Claims, No Drawings

DETECTION OF SPECIFIC ANTIGENS IN A POPULATION OF ANTIGENS

CROSS REFERENCE TO RELATED APPLICATIONS

This Application is a divisional application of U.S. patent application Ser. No. 13/385,428, now U.S. Pat. No. 9,182,389 B2 issued Nov. 10, 2015 entitled Detection of Specific Antigens in a Population of Antigens filed Feb. 21, 2012, which claims the benefit of U.S. Provisional Application Ser. No. 61/463,738 entitled Quantitative Fetal Maternal Hemorrhage Test, filed Feb. 22, 2011.

STATEMENT REGARDING FEDERALLY SPONSORED RESEARCH OR DEVELOPMENT (Not Applicable)

REFERENCE TO A SEQUENCE LISTING, A TABLE, OR A COMPUTER PROGRAM LISTING APPENDIX SUBMITTED ON COMPACT DISC (SEE 37 CFR 1.52(e)(5))
(Not Applicable)

BACKGROUND OF THE INVENTION

Field of the Invention

This invention relates to novel methods for detecting the presence or absence of, and for quantifying, one set of cells in a mixed cell population of at least two sets of cells wherein one set of cells has an antigen not found on the other set. It especially relates to such methods wherein one set of cells is Rh positive cells in a mixed population with Rh negative cells, as is found in a fetal maternal hemorrhage (FMH).

More particularly, it relates to performing the above procedures wherein the novel methods utilize gravitational forces or applying magnetic forces to reactive magnetic particles to isolate, distinguish and quantify cells differentiated by antigenic composition, such as Rh positive fetal cells, from Rh negative maternal blood cells, and especially for low populations of Rh positive cells in Rh negative maternal blood.

During pregnancy, the blood circulations of mother and baby are separate and do not mix. There is however, typically some level of leakage of small amounts of blood from the baby's circulation into the mother's circulation in almost every pregnancy. This is called Fetal Maternal Hemorrhage (FMH). Diagnostic tests to detect and measure the amount of baby's blood in the mother's blood sample can be very important to determine in the case of certain clinical circumstances, such as for example, when an Rh negative mother is pregnant with an Rh positive baby.

Fetal maternal hemorrhage (FMH) may occur both late in pregnancy and during delivery, and may cause Rh immunization of the mother and consequent Hemolytic Disease of the Fetus and Newborn in the mother's future Rh-positive babies. It is therefore very important to screen for and detect such occurrences to permit therapeutic intervention, if clinically indicated, to avoid future potential life-threatening events for potential future children of the subject mother.

The standard of care to prevent Rh iso-immunization and Rh Hemolytic Disease is to administer an Rh immune globulin (RHIG) product, such as RhoGAM®, manufactured by Ortho Clinical Diagnostics Inc., Raritan, N.J., to all Rh negative mothers at the time of risk of Rh immunization when FMH regularly occurs. To cover FMH, one dose (about 300 micrograms of RHIG) of a product such as RhoGAM, or a therapeutic dose of a similar product appropriate to the clinical circumstance, is typically administered to all Rh negative mothers at 28 weeks gestation. One or more additional doses, depending on the size of the FMH are administered after delivery if the subject baby is determined to be Rh positive. Occasionally, however, there may be large and even massive FMHs which must be detected and measured since in that case, multiple doses of RhoGAM or similar products would be necessary to prevent Rh immunization. One dose postpartum is considered to be necessary for each 15 ml (or part thereof) of Rh positive fetal red cells. This represents about 0.5% to 1.0% of the total maternal circulating red blood cells depending on the size of the woman, when the sample is from an average size woman with an average of 1500 ml of circulating RBC. The calculation of the percentage FMH is well within the skill of art.

It is standard medical practice to screen for potential FMH in all Rh Negative mothers after delivery of an Rh Positive baby using a diagnostic screening test to detect the FMH. If the screening test is positive, it is necessary to quantitate the size of the FMH so as to determine the number of doses of RhIG needed to cover the size of the FMH.

A currently commercially available screening test for FMH employs a "mixed field detection" methodology where the intent is to detect the baby's red blood cells in the mother's blood circulation by observing "rosettes", under the microscope, and counted by a technologist to screen for FMH. The sensitivity of the rosette test is such that it becomes positive with 10 ml of fetal cells in the mother's circulation, i.e. about 0.5% (based on 2000 ml of circulation $RB^2_s$). Once it is found to be positive a quantitative test is indicated.

A frequently used quantitative test for fetal RBCs in mother's blood is based upon the Kleihauer-Betke technique, whereby fetal cells are stained and manually physically counted to determine if the screening test result is positive. This Kleihauer-Betke method is considered to be sensitive to less than 0.1 ml of fetal cells in the mother's circulation and is quantitative. The Kleihauer-Betke test offers significant opportunity for improvement, however, since it is a manual, time-consuming procedure which requires a skilled technician with specialized training to conduct the test and to interpret the often ambiguous results which require subjective evaluation by the technician. Additionally, many have observed that the classic Kleihauer-Betke technique requires the use of certain reagents that are somewhat unstable in their shelf life and are said to be prone to false positive and false negative results. At best, due to variations in subjective results that potentially may occur among different technicians, results are considered to be imprecise and difficult to reproduce even among different trained technicians. Unfortunately, the combination of the screening test with the Kleihauer-Betke quantitative test fail to provide consistent results in the laboratory, Sandler, S. G. and S. Sathiyamoorthy. Laboratory Methods For Rh Immunoprophylaxis: A Review. Immunohematology, Journal of Blood Group Serology and Education. 2010, vol. 26, No 3, p 92-103).

Thus as the Sandler and Sathiyamoorthy publication demonstrates, there is an unmet need for a single, quantitative FMH test using a test principle that is rapid, economical and versatile and would perform both screening and quantitative functions with improved accuracy and reproducibility. The test should also deliver objective, numeric results free from the subjectivity inherent in the Kleihauer-Betke test in which a technologist counts rosettes observed in a defined microscopic field. Preferably, the new test would measure directly the volume of the fetal Rh positive cells in a sample of maternal blood of known volume and hematocrit.

A quantitative FMH test should accurately and reproducibly determine the volume of fetal Rh Positive red cells in the blood of an Rh Negative mother and thereby aid directly in determining the proper dose of Rh Immune Globulin (RHIG). Ideally, only one FMH test would be necessary on the subject patient and that test could serve as both a screening test to signify the occurrence of a large fetal hemorrhage and also, if such hemorrhage has occurred, it should quantify the extent of that hemorrhage.

A major difficulty in developing and providing such an FMH test stems from the fact that the fetal cells are usually a small fraction of the total maternal blood. These fetal blood cells can be present from as little as just above zero to 15% or so in the case of a massive exsanguination of a mature fetus. In the great majority of pregnancies, the FMH is less than 1%, i.e., the cutoff for administering more than one dose of Rh Immune Globulin. As noted, one dose is usually given prophylactically at 28 weeks gestation without requiring FMH screening at that time.

Identifying the fetal cells and quantifying them in relation to the maternal blood volume, requires that the diagnostic test performed on the Rh Negative mother's blood right after delivery, be able to detect a FMH over 1% of maternal blood volume, and then to quantitate the bleed to determine the amount of Rh Immune Globulin (RHIG) that is required to prevent Rh sensitization of the Rh Negative mother. Based upon an Rh Negative mother's average circulating packed red cell volume of 1500 to 2000 ml, an FMH of 15 ml, (the maximum FMH covered by one dose of Rh Immune Globulin), would give a reading of less than 1% i.e., about 0.75% on a quantitative test. One dose of Rh Immune Globulin is administered for every 15 ml of FMH measured. Since the use of FMH tests is related to determining the dosage of Rh Immune globulin suitable for the suppression of the immune response of the mother, probably the most important issue is the ability to quantitate a bleed accurately in the range of typically 0.5% (7.5 ml packed cells) up to about 15% (300 ml packed cells). For very rare larger bleeds a second assay using a smaller sample may be required.

BRIEF SUMMARY OF THE INVENTION

While the invention is described below in the context of the detection of FMHs, it is equally applicable for the detection of any cells differentiated by antigenic composition. We describe below several Rh incompatible FMH tests, creating and separating aggregates of Rh positive red cells gravimetrically and/or magnetically from a sample and isolating the aggregates for quantitation. (Note: "Rh positive" red cells are also referred to using different but accepted nomenclature as "D positive" red cells and similarly for Rh negative, or "D negative" red cells). The procedure involves using a test protocol that utilizes magnetic particles coated with anti-D, the Rh positive fetal cells (or "D positive" red cells) will bind to the anti-D coated magnetic particles and form micro to macro aggregates of the fetal Rh positive cells and the magnetically tagged anti-D. However, the Rh negative maternal cells will not be bound to the anti-D coated magnetic particles nor to aggregates that have formed with the RH positive fetal cells. Because of increased size, the Rh positive fetal cell aggregates will settle more rapidly than the non-aggregated maternal red cells according to Stokes Law. In addition, the aggregates contain paramagnetic particles which can accelerate the sedimentation of the aggregates under the influence of an appropriate magnetic force.

The aggregates containing the Rh positive cells and magnetic particles can then be separated from the maternal cells by application of a magnetic field, but the large concentration of maternal blood cells makes visualizing and quantifying the fetal cells difficult unless further separation steps to keep the maternal cells segregated away from the fetal cells are employed. Repeated washes with saline could be used to segregate the respective fetal and maternal cells but to do so may potentially cause loss of some of the aggregated fetal cells.

The methods of the present invention not only cause the aggregates to settle, but also provide techniques for pulling Rh positive red cell aggregates by magnetic force or gravity through a transparent or opaque separating solution into a measuring zone where the volume of Rh positive cells from the FMH can be measured.

Several variations of the invention involve reacting magnetic particles coated with anti-D antibodies with the Rh positive fetal cells in Rh negative maternal blood followed by a specific separation and quantifying technique. The Rh positive fetal cells will bind to the anti-D coated magnetic particles and form variously sized aggregates of the fetal Rh positive cells and the magnetically tagged anti-D. In addition, IgM anti-D and measured volumes of strongly reactive Rh positive cells to coaggregate with the fetal cells may be added to the reaction mixture to increase the aggregates, The Rh negative maternal cells will not be bound to the aggregates. The aggregates containing Rh positive fetal cells will settle more rapidly than the non-aggregated maternal red cells, but in accordance with the invention, the paramagnetic particles in the aggregates can be pulled through the mixture under the influence of an appropriate magnetic force, much faster than simple sedimentation would permit. The aggregates containing the Rh positive cells aggregated to the magnetic particles through the anti-D-coating so separated from the unreacted Rh negative maternal cells, are visualized and quantified by pulling the magnetic particles by magnetic force through a transparent separating solution into a measuring zone where the volume of Rh positive cells from the FMH can be measured. The extent of the FMH is obtained by using a quantitative method to determine the actual volume in the sample of the fetal Rh positive cells separated magnetically from the maternal Rh negative cells. This volume is then correlated to the volume of the original blood sample and expressed as a percentage of the maternal cell volume to give a quantification of the size of the bleed. The bleed size percentage is then an indication of the number of doses of RhIG needed to be administered to the mother to prevent subsequent Rh immunization.

Other variations of the invention do not involve magnetic particles and magnetic forces. They involve the addition of anti-D antibodies and known volumes of strongly reactive Rh positive cells to coaggregate with the Rh positive fetal cells in the sample. The manipulation of the maternal sample to creates large coaggregates containing Rh positive fetal cells which settle more rapidly than the nonaggregated maternal cells by gravity through a separating solution and into a separate zone where the aggregates are isolated, sedimented and the volume of the coaggregates determined. The volume of Rh positive fetal cells in the maternal sample is determined by subtracting the known volume of the strongly reactive Rh positive cells added to the reaction mixture and this volume is then correlated to the volume of the original blood sample and expressed as a percentage of the maternal cell volume to give a quantification of the size of the bleed. The bleed size percentage is then an indication of the number of doses of RhIG needed to be administered to the mother to prevent subsequent Rh immunization.

DETAILED DESCRIPTION OF THE INVENTION

Four versions of the invention are described which differ in the materials used to aggregate the Rh positive cells in the reaction mixture and move the aggregated cells to the volumetric graduated measuring zone. To aggregate the cells in the reaction mixture one method uses a reagent consisting of anti-D coated magnetic particles, the second method uses anti-D coated magnetic particles plus unbound complete agglutinating anti-D, typically IgM, the third method uses anti-D coated magnetic particles plus unbound complete agglutinating anti-D typically IgM plus a measured volume of strongly reactive Rh positive cells to coaggregate with the Rh positive cells in the sample, the final method is similar to the third method except the anti-D coated particle is either omitted, or if present, preferably has a high specific gravity. In the separation phase, the first, second and third method moves the aggregates with magnetic force, but in the fourth method the aggregates are allowed to settle or sediment by gravitational force.

The first version of the invention is based on the use of an appropriate number of small paramagnetic particles coated with anti-D to aggregate Rh positive fetal cells and impart a paramagnetic property to the aggregates. Preferably, the total number of magnetic particles used in the assay is typically larger than the number of fetal cells in the sample, although under some circumstances, a number of particles even lower than the number of fetal red blood cells in the sample is used. A preferred amount under many circumstances is from about $1 \times 10^7$ to about $5 \times 10^8$. Usually, however, the total volume (as opposed to number) of magnetic particles used in the invention is typically much smaller than the total volume of fetal red blood cells in the sample. Cellular staining reagents and microscope-based visual counting procedures are usually not required.

The invention usually starts with a volume of maternal packed red blood cells in a liquid mixture, from which the volume of total packed red cells (maternal cells plus fetal cells) is known or ascertainable. The liquid mixture can be, for example, blood, serum, plasma or saline. The actual sample size selected is well within the skill of the art. To that volume of packed red cells is added an appropriate amount of magnetic particles coated with anti-D antibody, the amount of magnetic particles usually being in excess of those sufficient to react with the expected volume of the Rh positive hemorrhage. The resulting mixture is incubated to allow the formation of a tagged complex of the anti-D particles with the Rh positive cells. Less than an excess of such particles may be used if desired, as will be discussed below. The aggregated complex is then pulled by magnetic force or gravity away from the Rh negative maternal cells through a transparent or opaque separating or wash solution into a reading zone and the volume of the magnetic particle complexed cells determined by a quantitative method. The volume of the particles in unreacted form may be subtracted from the total determined volume to arrive at a more precise result, but in general the particle volume is much less than the red cell volume and may be ignored as insignificant since the minimal volume addition errs on the side of the safety of the RhIG dosing of the mother. The volume of the aggregated cells is then expressed as a percentage of the total maternal red blood cell volume of the sample containing both Rh negative mother cells and Rh positive fetal cells, adjusted for the volume of the magnetic particles, if desired. The number of dosages of Rh immune globulin to be administered to the mother is then correlated with the FMH volume that is determined, as discussed above and hereinafter.

A critical component of one embodiment of the assay system is the paramagnetic particle anti-D reagent. This reagent imparts a paramagnetic field to the Rh positive red cells it reacts with under the influence of a magnetic field. It is also possible to add free IgM anti-D antibody to the assay system to participate in the aggregation process. The addition of measured quantities of free, complete IgM anti-D to the reaction is contemplated as a way to decrease the amount of the paramagnetic particle anti-D reagent which is usually an expensive reagent. By augmenting the paramagnetic particle anti-D reagent with free IgM anti-D, the quantitative range of the assay may be maintained or even expanded even though less Paramagnetic Particle Anti-D Reagent is used. In some aspects, this embodiment is preferred.

In the method of the invention, the aggregates settle and are magnetically moved into a separating vessel that contains a transparent or opaque separating fluid which will allow the aggregates to enter under magnetic propulsion but will also act as a barrier or partial barrier for the unreacted maternal red cells and prevent or impede their entry into the area. In the preferred embodiment, the separating device may also contain a graduated volumetric measuring zone into which the Rh positive cells are brought for quantification. The term "transparent" as used herein is meant to apply to the clarity of the separating solution in terms of its ability to permit visualization of the deposited complexes and aggregates by the naked eye. Thus, the term includes clear transparent solutions or suspensions as well as opaque liquids or suspensions in which the image of the deposit under the test conditions is discernible by the naked eye or by instrumentation in appropriate circumstances. The terms "transparent" and "opaque" are used interchangeably herein for this purpose. The terms "separating solution" and "wash solution" and similar variations thereof are intended to have the same meanings as set forth in the foregoing.

The assay thus has two phases, an incubation phase and a separation phase. The phases may be carried out in separate vessels or in the same vessel. In the incubation phase, a measured volume of a maternal sample of blood, usually in the form of measured packed cells, is mixed with anti-D coated paramagnetic micro beads. The number of paramagnetic microbeads is preferably in considerable excess to the number of fetal cells that would be expected in the sample. This mixture is incubated to allow the binding of the anti-D coating of the microbeads to all of the Rh positive fetal red cells in the maternal sample and the formation of micro aggregates to larger aggregates of the cells and paramagnetic beads. The formation of aggregates will aid in the separation of the fetal cells from the maternal cells which will settle slower than the aggregates. In most cases, the bulk of the maternal cells appear in the uppermost portion of the separation and do not impair reading of the deposited aggregates.

Following the incubation phase, if the incubation takes place separately from a suitable separating fluid, as is preferred, a portion of the sample or the entire sample is transferred into a separating device having a volume measuring zone containing a transparent or opaque separating fluid. The measuring zone preferably has graduated markings to facilitate measuring the volume of reacted Rh positive fetal cells. The separating fluid is capable of preventing unreacted Rh negative cells of the reaction mixture from entering the measuring zone during the period of separation and reading. By applying a magnetic force, or allowing gravity to act, as the case may be, the microaggregates of Rh positive cells, paramagnetic particles and reacted added IgM anti-D aggregates, are moved out of the reaction zone through the separating fluid away from the unreacted maternal red cells and into the graduated measuring zone. In the preferred embodiment, the microaggregates are all packed in the bottom of the graduated volumetric measuring zone, and the volume of the collected microaggregates is determined. This method provides a simple quantitative method to determine the volume of a fetal maternal hemorrhage and to permit determination of the proper dose of RhIG to be administered. Other quantitative methods may be employed.

When the reaction is carried out in a reaction vessel separate from the separating and reading tube, the procedure after incubation involves:
1—adding separating fluid to fill the bottom of the separating tube, approximately 0.5 to 1.0 ml in many procedures,
2—transferring the reaction mixture into the tube slowly to allow the mixture to layer on top of the separating fluid,
3—applying a magnetic field, if needed, located at the bottom of the tube. The Rh positive red cell/magnetic particle aggregates will migrate into the graduated reading zone.
4—determining the volume of packed Rh positive red cell aggregates in the lower portion of the tube.

If the reaction vessel and the separating/reacting tube are an integral set, the entire unit may contain the separating liquid, but care should be exercised in making certain the reaction mixture is well-mixed prior to and during incubation and the separating layer remains separate from the reaction mixture.

The following steps illustrate a general method of the present invention.

Step 1—Provide in a reaction vessel, a known amount of a maternal packed red blood cells sample in a diluent such as saline or plasma containing Rh bleed fetal cells and a suspension of small diameter, preferably 0.5 microns to 10 microns and most preferably 1 to 5 microns, anti-D coated, paramagnetic particle reagent having a known volume, and optionally, free agglutinating IgM anti-D antibody, Step 2—Incubate and mix the reaction mixture to allow the fetal cells, the coated magnetic particles and free IgM anti-D, if any, to form a complex and microaggregates, Step 3—Transfer the well-mixed reaction mixture to a separating device containing a transparent or opaque isotonic separating wash fluid preferably in a manner which results in a layering of the reaction mixture on the upper surface of the wash fluid.

Step 4—Move, or allow or cause the movement of, the paramagnetic particles and red cell aggregates into a volumetric measuring zone allowing the wash fluid, which is a separating solution to retard the entry of non-magnetized material such as unreacted maternal cells, into the zone, Step 5—Determine the packed volume of the packed fetal red cell/magnetic particle complex and aggregates in the volumetric measuring zone and if desired subtract the volume of the paramagnetic particle volume to determine the net packed fetal cell volume in the maternal blood sample.

Step 6—Determine the percentage of total fetal hemorrhage volume determined in Step 5 in the total sample and correlate that to RhIG dose needed to prevent Rh immunization. Techniques known in the art can be used to account for anticoagulants or other materials added to the reaction mixture, if desired.

Steps 1-5 above represent an effective screening test for FMH while the addition of Step 6 leads to quantification of the amount of RhIG dosage required.

From the foregoing, it will be seen that the method in one aspect thereof contemplates utilizing the following:

1) a reaction vessel for incubation and mixing of the reaction mixture, typically of 2-10 ml volume, 2) paramagnetic particles coated with anti-D antibody in excess to the expected FMH bleed, and optionally a free, complete agglutinating IgM anti-D antibody, 3) The separating isotonic wash fluid should be of sufficient specific gravity to retard the sedimentation of unreacted red cells of the reaction mixture as the aggregated complexes pass through it during the separation and reading phase. Typically, a specific gravity of greater than the specific gravity of the whole blood sample, but not greater than the specific gravity of red cells in the sample, is selected. Solutions of bovine serum albumin are suitable, especially those of about 8% to 11% concentration. Some Ficol® reagents are also suitable. FICOLL® is a neutral, highly branched, high-mass, hydrophilic polysaccharide which dissolves readily in aqueous solutions. FICOLL® radii range from 2-7 nm. It is prepared by reaction of the polysaccharide with epichlorohydrin. FICOLL® is a registered trademark owned by GE Healthcare Companies. The magnetic particles can have a specific gravity less than that of the wash fluid so that they would float when not bound to a cell, but would sediment as a part of the more dense red cell magnetic particle aggregates which have a greater specific gravity than the wash solution.

4) In the preferred embodiment, the separating device, or tube, preferably contains graduated markings to indicate a volumetric measuring zone filled with wash fluid. This separating device and volumetric measuring zone may be part of the reaction vessel, but are preferably separate. The separating vessel can contain both a separating fluid and the reaction mixture of typically less than 15 ml. The smaller the measuring volume graduations in the volumetric measuring zone the less sample required in the assay. For example, if the measuring volume graduations are 1 microliter, a packed cell volume of 100 microliters would be required to determine a 1% bleed, but if the measuring volume graduations are 10 microliters a packed cell volume of 1 ml would be required to determine a 1% bleed.

5) Appropriate red cell controls.

6) A source of a suitable magnetic field to move the magnetic particles and red cell aggregates or simply allowing gravity to move the particles.

The reaction vessel is utilized to provide the locus of the reaction between the Rh positive fetal cells in the maternal blood and the anti-D coating on the magnetic particles. Preferably, the paramagnetic particles will be in excess in number to the expected size of the bleed. Typically, it is preferred to use a maternal blood sample of between 0.2-1.5 ml of packed red cells from maternal blood samples of preferably 5-15 ml. This amount of sample will provide easily readable Rh positive bleed volumes of 0.1% to 15%, especially those less than 5%, and most preferably those from 0.4% to 3%, that may be normally expected postpartum in an Rh negative mother.

The second embodiment of the invention includes free, complete agglutinating anti-D antibody, typically IgM, in the assay reagent along with the anti-D coated magnetic particles to participate in the aggregation process of Step 1. The addition of measured quantities of free, complete IgM anti-D to the reaction is contemplated as a way to decrease the amount of the paramagnetic particle anti-D reagent which could be both an expensive reagent and may not impart the additional desired binding characteristics obtained with IgM antibody. By augmenting the paramagnetic particle anti-D reagent with free anti-D, the quantitative range of the assay may be maintained or even expanded even though less paramagnetic particle anti-D reagent is used. Sufficient anti-D magnetic particles are in the reagent to bind in the cell aggregates and move the complex. The difference between this embodiment and the first embodiment described herein above, is that in the first embodiment all Rh positive cells are bound to a paramagnetic particle and form aggregates, whereas in this second embodiment only some of the aggregated cells have paramagnetic particles attached directly to them since both the coated paramagnetic particles and the free IgM antibody are aggregating the cells. The general method for such an embodiment would be described as follows:

Step 1—Provide in a reaction vessel, a known amount of maternal blood sample containing Rh positive bleed fetal cells and a reagent comprising a suspension of small diameter, anti-D coated, paramagnetic particles having a known volume, and free unbound complete agglutinating anti-D in solution, Step 2—Incubate the reaction mixture to allow the fetal cells and the coated magnetic particles and complete agglutinating anti-D to form aggregate and microaggregate complexes, Step 3—Transfer the well-mixed reaction mixture to a separating device containing a transparent or opaque isotonic separating solution.

Step 4—Apply a magnetic field to move the paramagnetic particles and red cells aggregated therewith into the graduated volumetric measuring zone allowing the separating solution to retard the entry of non-magnetized material such as unreacted maternal cells into the zone.

Step 5—Determine the packed volume of the packed fetal red cell/magnetic particle and antibody complex. In the preferred embodiment, this is done in the graduated volumetric measuring zone and optionally subtract or ignore the volume of the paramagnetic particle volume to determine the net packed fetal cell volume in the maternal blood sample. Typically, the packed volume of the Rh positive cell aggregates and complexes will range from about 1 to 40 microliters.

Step 6—Calculate the maternal blood RBC volume using known techniques and calculate the percentage of total fetal hemorrhage volume such as by dividing it by the total maternal blood volume. Techniques known in the art can be used to account for anticoagulants or other materials added to the reaction mixture, if desired.

The size of the anti-D coated paramagnetic particles is selected to enable the complex of red cells with paramagnetic particles attached to move in a magnetic field strength normally used in magnetic assay laboratory procedures toward the magnet used in the method of the invention. For example, paramagnetic particles sized about 1 to 5 microns diameter, are commercially available having a volume that is a small fraction of the volume of the approximately 7-8 micron diameter biconcave red cells which is about 90 fl. (about 90 cubic microns). A 3 micron sphere has a volume of 14 fl, a 2 micron sphere has a volume of 4.17 fl, a 1.5 micron sphere a volume of 1.75 fl, and a 1 micron sphere a volume of about 0.5 fl. Thus, the red cell, with its volume of 90 fl, has about 6.5 times the volume of the 3 micron paramagnetic particles. In the invention, it is preferred to use paramagnetic particles which are 1-5 microns in diameter. The objective of this is to use particles that do not contribute significantly to the volume of the red cells aggregates to which they are attached yet impart a magnetic property that can cause the aggregates to move in a magnetic field.

Another embodiment of the invention includes free, complete agglutinating anti-D antibody, typically IgM, in the assay reagent along with the anti-D coated magnetic particles and a second reagent a suspension of a measured volume of strongly reactive Rh positive cells, for example, a suspension of 10 microliters of $R_2R_2$ cells which may have been enzyme treated, to participate in the aggregation process. The addition of measured quantities of free, complete or IgM anti-D to the reaction is contemplated as a way to decrease the amount of the paramagnetic particle anti-D reagent which is an expensive reagent. By augmenting the paramagnetic particle anti-D reagent with free anti-D, the quantitative range of the assay may be maintained or even expanded even though less Paramagnetic Particle Anti-D Reagent is used. Sufficient anti-D magnetic particles are in the reagent to bind in the cell aggregates and move the complex. The addition of strongly reactive Rh positive cells will strongly coaggregate with any Rh positive cells in the sample, by adding mass to the aggregates so that they will settle faster by gravity, and be an internal control that creates a minimal volume in each assay (i.e. 10 microliters). Steps 1 through 6 as described above are followed except as modified below:

Step 1—Provide in a reaction vessel, a known amount of maternal blood sample containing Rh bleed fetal cells and a reagent comprising a suspension of small diameter, anti-D coated, paramagnetic particles having a known volume, and free unbound complete agglutinating anti-D in solution and a known volume of strongly reactive Rh positive cells such as $R_2R_2$ cells, Step 2—Incubate the reaction mixture to allow the fetal cells and the coated magnetic particles and complete agglutinating anti-D and strongly reactive Rh positive cells to form aggregate and microaggregate complexes, Step 3—If the reaction, mixture was not performed in the presence of a dense transparent isotonic wash solution, transfer the well-mixed reaction mixture to a separating device containing such a solution, Step 4—Apply a magnetic field to move the paramagnetic particles and red cells aggregated therewith into the graduated volumetric measuring zone allowing the separating solution to retard the entry of non-magnetized material such as unreacted maternal cells into the zone.

Step 5—Determine the packed volume of the packed fetal red cell/magnetic particle and antibody complex. In the preferred embodiment, this is done in the graduated volumetric measuring zone and subtract the volume of the strongly reactive Rh positive cells (i.e. 10 microliters) and optionally subtract or ignore the volume of the paramagnetic particle volume to determine the net packed fetal cell volume in the maternal blood sample.

Step 6—Calculate the maternal blood RBC volume using known techniques and calculate the percentage of total fetal hemorrhage volume such as by dividing it by the total maternal blood volume. Techniques known in the art can be used to account for anticoagulants or other materials added to the reaction mixture, if desired.

Another embodiment of the invention includes the use of free complete agglutinating anti-D antibody, typically IgM, in the assay reagent and a second reagent a suspension of a measured volume of strongly reactive Rh positive cells, for example a suspension of 10 microliters of $R_2R_2$ cells which may have been enzyme treated, to participate in the aggregation process. The free complete agglutinating anti-D will form large aggregates with the Rh positive cells in the sample and the strongly reactive Rh positive cells. The addition of strongly reactive Rh positive cells will strongly coaggregate with any Rh positive cells in the sample, add mass to the aggregates so they will settle faster by gravity, and third be an internal control that creates a minimal volume in each assay (i.e. 10 microliters).

In the following iteration, magnetic particles are not required in the reaction mixture and a magnetic field is not used to pull down on the aggregates.

Step 1—Provide in a reaction vessel, a known amount of maternal blood sample, free unbound complete agglutinating anti-D in solution and a known volume of strongly reactive Rh positive cells, Step 2—Incubate the reaction mixture to allow the fetal cells, complete agglutinating anti-D and strongly reactive Rh positive cells to form aggregate and microaggregate complexes, Step 3—Transfer the well-mixed reaction mixture to the separating device containing a relatively dense separating fluid or solution as was shown in a previously described embodiment, Step 4—Allow the red cells aggregates to settle or be sedimented into the graduated volumetric measuring zone allowing the separating solution to retard the entry of nonaggregated maternal cells into the zone. The specific gravity of the separating solution under these circumstances is usually about the same as the Rh negative cells and the aggregates. The aggregates however, will settle faster than the unreacted materials. When the aggregates are sufficiently separated from the nonaggregated cells a plug may be inserted into the tube between the aggregated cells and the nonaggregated cells and the tube centrifuged to compact the aggregated cells in the graduated reading zone. Nonaggregated cells will sediment above the plug.

Step 5—Determine the packed volume of the packed fetal red cell and antibody complex. In the preferred embodiment, this is done in the graduated volumetric measuring zone and subtract the volume of the strongly reactive Rh positive cells (i.e. 10 microliters) to determine the net packed fetal cell volume in the maternal blood sample.

Step 6—Calculate the maternal blood RBC volume using known techniques and Calculate the percentage of total fetal hemorrhage volume such as by dividing it by the total maternal blood volume. Techniques known in the art can be used to account for anticoagulants or other materials added to the reaction mixture, if desired.

The preferred method of measuring the volume of the fetal bleed according to the invention is to direct the separated fetal cell/magnetic particle into a tube having graduated markings indications volume present on the tube. The packed cells can then be measured directly in the tube via the graduated markings. Virtually, any method for measuring volume may be employed, however, and thus, in a broad aspect of the invention, the volume of the fetal cells recovered in the method is simply described as being determined and expressed as a percentage of the total volume of the maternal red blood cells. When paramagnetic particles are not used in the assay and the aggregated cells settle through the separating solution by gravity, after a sufficient time has elapsed to separate the aggregates from the nonaggregated cells, a plug can be inserted into the separating tube at the point where the tube narrows, to divide the upper part of the tube and the settled material into two zones. After the plug is inserted, the aggregated cells can be rapidly brought to the bottom of the tube by centrifugation in order to determine the aggregated cell volume. The nonaggregated cells will sediment above the plug.

Graduated tubes useful in the invention are well-known in the art. One such tube is the KIMAX®, graduated Hopkins vaccine centrifuge tube [available from General Laboratory Supply, Pasadena, Tex. 77503, www.gogenlab.com]. Such a tube has no blue markings in 0.01 ml increments from the lower end up to a volume of 0.05 ml at the narrow lowermost end of tube. The tube begins to widen gradually at about 0.08 ml and then has markings at 1 ml, 5 ml and 10 ml graduations thereafter in the expanded area of the tube. Such a tube is suitable for conducting the present invention. A preferred device however, which would allow for the use of smaller samples, for the present invention would be one of molded plastic having a gradually decreasing diameter in the lower area with typically 0.01 ml graduations in that area. Finer volume indications would be beneficial and could lead to smaller sample volumes. The volume of separating solution used in such a tube is preferably about 0.75 ml to about 1.0 ml. When it is desired to separate the unreacted materials in the reaction mixture from the separated and segregated aggregates in the separation solution, it is possible to insert a plug in the area between the interface of the reaction mixture and the separating solution and then submit the resulting configuration to centrifugation to allow the materials in the separating solution to settle further into packed aggregates.

The method of the invention lends itself to the provision of a kit of components which are each packaged and used for various embodiment of the invention. For example, kit components include any combination of two or more of the following:

1. Reagent "A":
    a) Anti-D Reagent (monoclonal or polyclonal) in solution alone or coated onto magnetic particles
    b) Magnetic particles alone or coated with anti-D Reagent
    c) IgM anti-D antibody (free, complete, agglutinating antibody)
2. Reagent "B": Separating Solution
3. Reagent "C": a suspension of strongly reactive Rh positive cells e.g. $R_2R_2$,
4. Reaction tubes and volumetric reading tubes
5. Tube rack with magnetic field component integrated into the rack, magnets positioned so as to be under the reading end of the reading tube, provided that the kit contains at least volumetric reading tubes, components 1a) and 1b) from reagent A above and reagent B.

The preferred anti-D material is a monoclonal anti-D antibody coated onto the paramagnetic particle in the manner well-known in the art. Polyclonal anti-D may be used as well, though this is not preferred. IgM anti-D is preferred when magnetic particles are not used.

The separating solution, as previously noted above, is a transparent liquid having a specific gravity of usually greater than 1.0 and is selected for its ability to allow unreacted maternal cells to remain suspended or float on top of the separation liquid as opposed to settling out of the liquid. Appropriate dilutions of serum albumin, e.g., bovine serum albumin, serve well for this purpose.

The paramagnetic particles are Dynabeads® obtainable from Invitrogen (Life Technologies, Carlsbad, Calif.).

While the foregoing descriptions and embodiments have been provided with respect to the presence of Rh positive cells in a larger population of the Rh negative cells, the invention has broader applicability as noted above. For example, another application is to detect antibodies or antigens on platelets, or on white blood cells with adjustment of the specific gravity of the separating solution using an appropriate antibody specific to the cell population of interest.

There are many examples of assays that utilize cell-sorter instruments to identify a given red cell, white cell or platelet population which could also be identified using the method of the invention (with relevant antibodies to the rare cells).

Other tests include measurement of cell survival with time, various treatment monitoring applications such as for patients with HIV, autoimmune diseases, leukemia, lymphoma and other maladies for which response (or lack thereof) to therapy is of clinical interest, provided appropriate antibodies are, or become, available.

Still others occur in immunohematology. For example, the methodology described in this application for fetal maternal hemorrhage detection can also be readily adapted for use in another critical blood bank application, for blood grouping and red cell antibody testing, the standard set of pretransfusion immunological tests of patients and donors performed by blood banks. These standard tests are ABO forward and reverse typing, Rh typing, red cell antibody screening and crossmatch. In this pretransfusion test system proposed here, the principle depends on RBC agglutinates in suspension, according to Stokes Law, sedimenting much more rapidly than free RBC in suspension.

The method of all standard pretransfusion tests is to incubate patient or donor red cell suspensions with patient or donor sera, or with red cell antibody reagents, to cause the RBC to agglutinate or become coated with antibody. If test RBC become coated with antibody during incubation, it is a positive test. If they remain uncoated, it is a negative test. RBC coated with "complete", "immediate spin", red cell antibodies will form agglutinates by "direct agglutination" during incubation. RBC coated with "incomplete" red cell antibodies will not form agglutinates during incubation but may become coated with antibody. It requires anti-human immunoglobulin (Coombs) reagent in the medium, in the absence of free human immunoglobulin, to agglutinate them by "indirect agglutination". Incubation may be performed in the same vessel on top of the clear separation fluid, or in a separate vessel and transferred for the sedimentation and reading step as is described above.

In positive tests where agglutination occurs during incubation in a positive test the agglutinates will sediment more rapidly than the free red cells of a negative test into the clear zone below and will have a characteristic optical pattern. In negative tests the free red cells enter the clear zone slowly and have a different cloud like optical pattern. Then rate of sedimentation will differentiate positive from negative tests. Rate of sedimentation can be enhanced by adjustments to the specific gravity and or viscosity of the suspension medium.

To perform an indirect antiglobulin test required for incomplete antibodies that coat but do not agglutinate RBC, the clear separating medium has human antiglobulin reagent added to it. Specific gravity of the clear separating fluid is set to be less dense than red cells and more dense than serum proteins so as to, by flotation, stop serum proteins from following with the red cells and neutralizing the anti-human antibody reagent there. As free coated red cells sediment into this region they will be agglutinated by the human antiglobulin reagent. Agglutinates will sediment more rapidly, according to Stokes Law, thus clearly differentiating agglutinated coated reds cell from unagglutinated uncoated red cells. Again, fast sedimentation indicates a positive test, slow sedimentation a negative test. Methods that cause mixing during this sedimentation may be used to enhance agglutination. Controls can be run by with O Rh Neg cells to establish the sedimentation rate of unagglutinated cells, in a separate test vessel or even by adding O Rh Neg cells to the incubation mixture in the same vessel.

Variations of the method include employing anti-A, anti-B and anti-D reagent antibodies tagged with magnetic particles, and reagent A, B, and O red cells tagged with magnetic particles, and then using magnetic force to move them into the clear zone below the incubation mixture for reading, to shorten test time. Or even to use reagent antibodies, and reagent red cells, tagged with heavy nonmagnetic particles to enhance the force of gravity.

Another variation is to employ centrifugation to speed up the rate of RBC sedimentation so as to obtain test results sooner. Reading is done by observing how fast RBC sediment from the incubating mixture into and down through the clear separating solution below. The simplest reading method is to set a timer when sedimentation begins and record the time in minutes of first arrival of RBC at the bottom of the test vessel. This method of reading also has the advantage of estimating strength of agglutination, 1+ to 4+, as stronger antibodies will cause stronger agglutination and faster sedimentation with shorter times of arrival. Other reading methods to differentiate a positive from a negative result comprise optical observation of the clear zone to measure speed of red cell settling, or recognize the optical pattern of agglutination in the sedimenting RBC.

The chief benefits of this system in an automated blood grouping and red cell antibody detection instrument are its simplicity and the lack of need for a robotic centrifuge.

The advantages of the invention include its potential availability in multiple settings such as small community hospitals, doctor's offices, as "stat" techniques for the large institution, and bedside testing immediately after drawing the specimen whereby no associated sophisticated and/or costly instrumentation (or even electricity) is required to accomplish the desired assay.

The following example will illustrate various aspects of the invention.

EXAMPLE

Prepare a Reagent comprising IgG anti-D coated paramagnetic microspheres and free IgM anti-D antibody.

Provide Dynabeads®, M-280 Sheep anti Mouse IgG obtained from Invitrogen Corporation, a unit of Life Technologies, Carlsbad, Calif. and Anti-D (Monoclonal Blend) Gamma-clone, a blend of two human/murine heterohybridomas from Immucor, Atlanta, Ga. The IgM is GAMA401 and the IgG is F8D8.

Coat the Dynabeads® with the Anti-D (Monoclonal Blend) and adjust the concentration to approximately $3.5 \times 10^8$ Dynabeads/ml suspension.

1—Prepare four separate 12% suspensions of mixtures of Rh negative red cells in saline containing Rh positive cells (as shown below) in four separate 12 mm×100 mm test tubes. Place 0.5 ml of suspension in each tube. The four suspensions will simulate four levels of FMH bleeds after the addition of the Rh positive cells. The first suspension contains only Rh negative cells (zero bleed). The second suspension contains 3 microliters of Rh positive cells in the cell mixture. The third contains 10 microliters of Rh positive cells in the separation and the fourth contains 20 microliters of Rh positive cells in the suspension.

2—Add 200 microliters of the suspension described above containing the coated Dynabeads® to each of the four test tubes.

3—Cap the test tubes and mix each suspension by rocking. Incubate at room temperature for 30 to 60 minutes.

4—Take four graduated Hopkins Vaccine centrifuge tubes as described above, label them to correspond to each of the cell suspensions, and add 0.8 ml of 70% separating solution of approximately 8%-11% isotonic bovine albumin solution to each test tube. The graduated tubes have a total capacity of 10-15 ml.

5—Using a pipette, layer each of the cell suspensions on top of the separating solution in the corresponding graduated volume tube.

6—Place each of the four tubes over a magnet, apply the magnetic field and let stand until the aggregated cells are in the bottom of each tube (approximately 5 minutes).

7—The volume of red cell aggregates in the bottom of the graduated tubes is then read and shows the following:

The first tube had no red cell aggregates and therefore corresponded to a zero (i.e. negative) bleed. Whether or not any of the magnetic Dynabeads® are pulled down in any negative depends upon the strength of the magnetic field and the specific gravity of the separating solution relative to the beads. With the strength of the magnetic field used herein, the coated beads remained in the reaction mixture or on the surface thereof. The second tube contained a volume of aggregates of 3 microliters corresponding to the 3 microliters of Rh positive cells added to tube 2. The third tube contained a volume of red cell aggregates of 10 microliters corresponding to a bleed of that size, and the fourth tube contained a volume of red cell aggregates of 20 microliters corresponding to a bleed of that size. Thus, each tube contained the level of Rh positive cells introduced into its respective sample at the start of the test.

From the foregoing, it is seen that the method of the invention is able to yield the volume of aggregates which corresponds to the known volume of Rh positive cells in a sample. Using the above technique, bleeds occurring over the range of expected values in maternal blood are easily determined via the appropriate adjustment of sample sizes. Thus, the above procedure is followed to produce a determined volume of aggregates obtained from various levels of known Rh positive volume bleeds in maternal blood, and noting the lines of demarcation on the volumetric reading zone of the measuring tube which correspond to the known Rh positive volumes. These points are then preserved to determine the Rh positive bleed levels in unknown maternal Rh negative blood suspected of containing an Rh positive bleed. The correlation between the bleed and RhIG dosage required can then be determined in the manner described previously herein, by those skilled in the art.

What is claimed is:

1. A method for detecting the presence or absence and optionally, the volume, of Rh positive cells in a liquid blood cell sample comprising Rh negative cells from an Rh negative woman suspected of containing Rh positive cells and suspected of requiring the administration of a dose of an Rh immunoglobulin to prevent a future Rh immunization which comprises:
   a) providing in a reaction vessel a liquid mixture comprising:
      1) a blood cell sample from said Rh negative woman suspected of containing Rh positive cells therein to be detected, and
      2) magnetic particles tagged with an agglutinating anti-D antibody reactable with the Rh positive cells sought to be detected and capable of forming a complex with said Rh positive cells, if present,
   b) incubating and mixing said liquid mixture to allow said Rh positive cells, if present, to react with said agglutinating anti-D antibody of said magnetic particles to form complexes and aggregates therewith in said liquid mixture, to form an incubated liquid reaction mixture in said reaction vessel,
   c) contacting said incubated liquid reaction mixture to a transparent or opaque separating solution contained in a test vessel,
   d) moving said aggregates and complexes, if formed in step b) above, through said separating solution by applying a magnetic field from a magnetic source and moving said aggregates and complexes to a site in said test vessel comprising an Rh positive cell volume measuring zone, at which the presence or absence, and optionally, the volume, of said aggregates and complexes, when formed, may be determined in said test vessel at said Rh positive cell volume measuring zone when the optional determination of the volume of said aggregates and complexes is selected, said separating solution being configured to retard the speed of movement of unreacted maternal Rh negative cells compared to the speed of movement of said complexes and aggregates,
   e) visualizing the separating solution at said Rh positive cell volume measuring zone to detect the presence of formed cell aggregates and complexes if said Rh positive cells are present in said blood cell sample or the absence of formed cell aggregates and cell complexes if said Rh positive cells are absent from said blood cell sample, and optionally measuring the volume of said Rh positive cells, if present at said Rh positive cell volume measuring zone when the optional determination of the volume of said formed aggregates and complexes is selected, wherein the volume of said Rh positive cells is used as the basis for the administration of a dose of an Rh immunoglobulin to said Rh negative woman to prevent a future Rh immunization.

2. The method of claim 1 which comprises in step e) thereof, performing the additional step of measuring the volume of said Rh positive cells aggregates and complexes and relating said volume as the basis to the required dosage of Rh immunoglobulin to be administered to said Rh negative woman to prevent a future Rh immunization.

3. The method of claim 2 wherein the contacting recited in step c) is performed in a separate test vessel from the reaction vessel.

4. The method of claim 3 wherein the incubated reaction mixture is layered over the separating solution in step c) thereof.

5. The method of claim 4 wherein the separate test vessel has graduated volume markings in the area of the Rh positive cell measuring zone in which formed aggregates and complexes are to be measured.

6. The method of claim 5 wherein the separating solution has a specific gravity lower than the specific gravity of said aggregates.

7. The method according to claim 5 wherein the Rh positive cells comprise up to about 15% of the total cell volume of the sample.

8. The method according to claim 5 wherein the separating solution comprises bovine serum albumin.

9. The method of claim 8 comprising the additional steps of inserting a plug between the separating solution and the incubation reaction mixture in said test vessel and submitting the test vessel to centrifugal force.

10. The method of claim 5 wherein the anti-D antibody comprises an IgM antibody.

11. The method of claim 10 wherein in step 2), a known volume of strongly reactive Rh positive cells is added to co-aggregate with the Rh positive fetal cells potentially present in said blood cell sample.

12. The method of claim 1 wherein in step e) thereof, Rh positive cells are absent and the optional determination of the volume of Rh positive cells is not performed.

13. The method of claim 12 wherein the contacting recited in step c) is performed in a separate test vessel from the reaction vessel.

14. The method of claim 13 wherein the incubated reaction mixture is layered over the separating solution in step c).

15. The method of claim 14 wherein the separating solution comprises bovine serum albumin.

16. The method of claim 15 wherein the anti-D antibody comprises an IgM antibody.

17. The method of claim 16 wherein in step 2), a known volume of strongly reactive Rh positive cells is added to co-aggregate with the Rh positive fetal cells potentially present in said blood cell sample.

* * * * *